United States Patent
Marshall et al.

(10) Patent No.: US 9,238,111 B2
(45) Date of Patent: Jan. 19, 2016

(54) PEN NEEDLES AND NEEDLE CAP ASSEMBLIES

(75) Inventors: Jeremy Marshall, Oxford (GB); Jessica Robson, Oxford (GB)

(73) Assignee: OWEN MUMFORD LIMITED, Woodstock (GB)

( * ) Notice: Subject to any disclaimer, the term of this patent is extended or adjusted under 35 U.S.C. 154(b) by 372 days.

(21) Appl. No.: 13/258,208

(22) PCT Filed: Apr. 19, 2010

(86) PCT No.: PCT/GB2010/000783
§ 371 (c)(1), (2), (4) Date: Nov. 17, 2011

(87) PCT Pub. No.: WO2010/119271
PCT Pub. Date: Oct. 21, 2010

(65) Prior Publication Data
US 2012/0071835 A1    Mar. 22, 2012

Related U.S. Application Data

(60) Provisional application No. 61/175,570, filed on May 5, 2009.

(30) Foreign Application Priority Data

Apr. 17, 2009    (GB) .................................. 0906640.8

(51) Int. Cl.
*A61M 5/32* (2006.01)
*A61M 5/34* (2006.01)
*A61M 5/24* (2006.01)

(52) U.S. Cl.
CPC ........... *A61M 5/3202* (2013.01); *A61M 5/3213* (2013.01); *A61M 5/3293* (2013.01); *A61M 5/347* (2013.01); *A61M 5/24* (2013.01); *A61M 2205/586* (2013.01)

(58) Field of Classification Search
CPC ............ A61M 5/3202; A61M 5/3213; A61M 5/3293; A61M 5/347; A61M 2205/586; A61M 5/3215; A61M 5/3204; A61M 39/20
USPC .......................... 604/240–243, 263, 199, 256
See application file for complete search history.

(56) References Cited

U.S. PATENT DOCUMENTS 2,564,804 A * 8/1951 Everett ........................... 285/38
4,288,657 A    9/1981 Swanson
(Continued)

FOREIGN PATENT DOCUMENTS

| EP | 1384491 | * | 1/2004 | ........... A61M 39/04 |
| JP | 2003267419 | * | 9/2003 | |
| WO | 2004052432 | | 6/2004 | |

OTHER PUBLICATIONS

Translation—JP2003267419 (machine translation from Espacenet, accessed on Jan. 18, 2014).*

(Continued)

*Primary Examiner* — Aarti B Berdichevsky
*Assistant Examiner* — Laura Schell
(74) *Attorney, Agent, or Firm* — Young & Thompson

(57) ABSTRACT

A pen needle or pen needle cap assembly is designed to be manually attached e.g. by screwing onto an injection device, and is provided with a gripping region designed to allow the torque that can be applied in the tightening sense to be less than that which can be applied in the loosening sense.

19 Claims, 3 Drawing Sheets

(56) References Cited

U.S. PATENT DOCUMENTS

| | | | |
|---|---|---|---|
| 4,883,921 A | | 11/1989 | Legerius et al. |
| 5,557,069 A | | 9/1996 | Whitehead et al. |
| 5,591,143 A | * | 1/1997 | Trombley et al. ............. 604/534 |
| 6,520,935 B1 | | 2/2003 | Jansen |
| 6,551,286 B1 | * | 4/2003 | Claessens .................... 604/263 |
| 7,544,191 B2 | * | 6/2009 | Peluso et al. ................. 604/414 |
| 8,435,258 B2 | * | 5/2013 | Young et al. ................. 606/169 |
| 2006/0032769 A1 | * | 2/2006 | Erickson et al. ............. 206/365 |
| 2009/0069753 A1 | * | 3/2009 | Ruan et al. ................... 604/192 |
| 2010/0094260 A1 | * | 4/2010 | Cude et al. ................... 604/533 |

OTHER PUBLICATIONS

International Search Report, dated Jul. 7, 2010 in corresponding PCT application.

Search Report dated Aug. 28, 2009, in corresponding Foreign application.

Japanese Office Action, dated Sep. 30, 2014 in corresponding JP application 2014-505231.

* cited by examiner

PEN NEEDLES AND NEEDLE CAP ASSEMBLIES

The present application is a U.S. National Phase application pursuant to 35U.S.C. §371of International Application No. PCT/GB2010/000783filed Apr. 19, 2010, which claims the benefit of U.S. Provisional Application No. 61/175,570, filed May 5, 2009.

This invention relates to a needle cap assembly comprising a pen needle and a removable needle cap as well as to pen needles per se.

A number of medical conditions such as insulin-dependent diabetes require a user to prepare an autoinjection device containing a cartridge of medication by screwing onto the front end of the device or cartridge a single use pen needle. Upon completion of the injection the pen needle is removed by unscrewing. The pen needle typically comprises a moulded plastics hub with an internal thread and a double ended needle with a rearwardly facing end designed to penetrate a septum in the end of the cartridge and a forward end for penetrating the flesh of a user. In order to reduce the pricking sensation and make the injection operation as comfortable as possible, the needles are of very fine gauge. Also the moulded plastics hub is fairly robust but should not be mishandled. In typical conventional arrangements the pen needle is supplied in a needle cap which is sealed by a foil seal which is peeled off prior to offering the pen needle up to the threaded end of the device or cartridge. The needle cap acts as a spanner to allow the pen needle to be screwed on and later unscrewed after use without the forward part of the needle being exposed. The cap is provided with a number of radially outwardly extending ribs and we have found that it is possible for a user to over-tighten it with potential damage to the hub and/or needle. Also, if the pen needle is over-tightened it can prove difficult to remove, particularly if the needle hub has been left on since the last usage. This is potentially dangerous as the user may be tempted to use excessive force and/or inappropriate tools to remove the pen needle and thus expose themselves to the risk of needle stick injury.

Accordingly, in one aspect, this invention provides a needle cap assembly for an injection device, the assembly comprising:
- a pen needle having an internal bore for being rotatably engaged with the injection device or an associated component, and having a forwardly projecting needle,
- a needle cap removable from said pen needle,
- the pen needle and the needle cap having complementary drive surfaces to allow rotation of the needle cap to be transmitted to said pen needle,
- wherein said needle cap is provided with an external differential torque transfer region.

Preferably said transfer region is a gripping region designed so that, when gripped manually in use, the torque that can be applied to tighten the needle cap (and thus the pen needle) before the manual grip slips is less than that which can be applied to loosen the needle cap.

One of the several advantages of this arrangement is that the twisting action is applied typically through the fingers of the user who will tighten the assembly by feel and so the torque applied is controlled by the patient fitting the needle. This is particularly beneficial because the same needle will be supplied for a number of different manufacturers' devices, and although there is a broad specification for the thread form there will be variations in thread profile depending on the method of formation and the particular material and so there will be different torques needed to fully screw home the pen needle (required for accurate dosage delivery), due to friction values varying from device to device.

Preferably said gripping region comprises a plurality of ribs spaced angularly around the needle cap, each rib having a generally smooth, relatively low friction surface facing the loosening direction. The low friction surface on each rib may be curved. Advantageously some or all of said ribs have a relatively high friction surface facing in the tightening direction. The relatively high friction surface may extend generally radially, and it may be plain or textured e.g. grooved or corrugated. Conveniently, said needle cap comprises a generally cylindrical base portion that merges with a generally frustoconical portion with a reduced diameter apex, and the ribs may be provided on at least the frustoconical portion. The frustoconical portion may be a surface of revolution of a line inclined towards the axis of revolution. The line may be straight or, more preferably, curved.

In another aspect there is provided a pen needle for being rotatably engaged with an injection device or an associated component in use, and having a forwardly projecting needle, wherein said pen needle includes an external differential torque transfer region.

Preferably said transfer region is a gripping region designed so that, when gripped manually, the torque that can be applied to tighten the pen needle before the manual grip slips is less than that which can be applied to loosen the pen needle.

The pen needle may be provided with one or more of the features set out above.

Whilst the invention has been described above, it extends to any inventive combination of the features set out above, or in the following description or claims.

The invention may be performed in various ways, and, by way of example only, two embodiments thereof will now be described, reference being made to the accompanying drawings in which.

Figure 1:
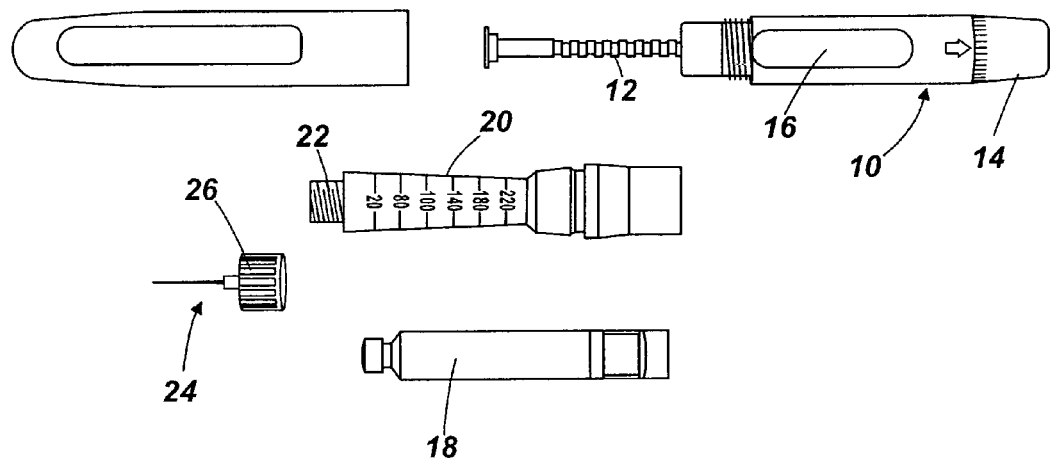
FIG. 1 is an exploded view of a pen-type autoinjection device for being loaded with a cartridge containing several doses of medicament delivered through a single use pen needle.
Figure 7:
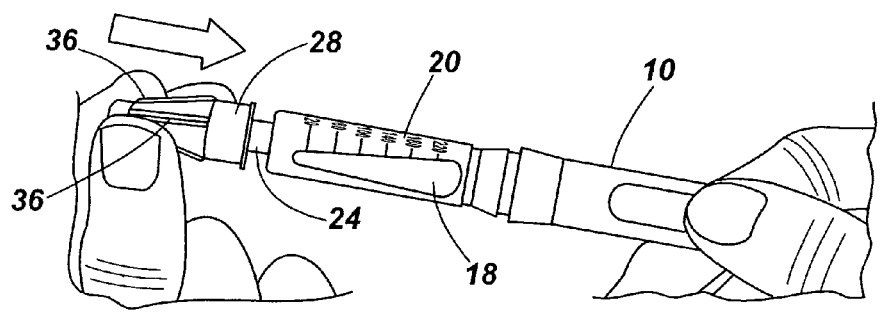
FIG. 7 shows an embodiment of this invention in use.

Referring initially to FIG. 1, the autoinjector comprises a pen body 10 containing a drive mechanism (not shown) which advances an internal plunger 12 axially by an amount determined by the dose dialled in via the dose selector 14, when the drive mechanism is released by pressing the release button 16. A multi-dose cartridge 18 can be loaded axially into a cartridge holder 20 which is then screwed onto the pen body. At the forward end of the cartridge holder 20 is a threaded portion 22 onto which a pen needle 24 having a double ended needle may be screwed. The rear end of the needle projects rearwardly and penetrates a septum in the front end of the cartridge when the needle is screwed home.

Figure 2:
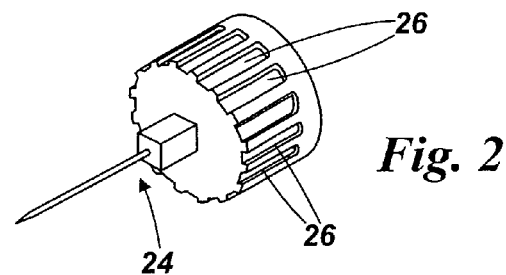
FIG. 2 is a general perspective view of a pen needle.
Figure 3:
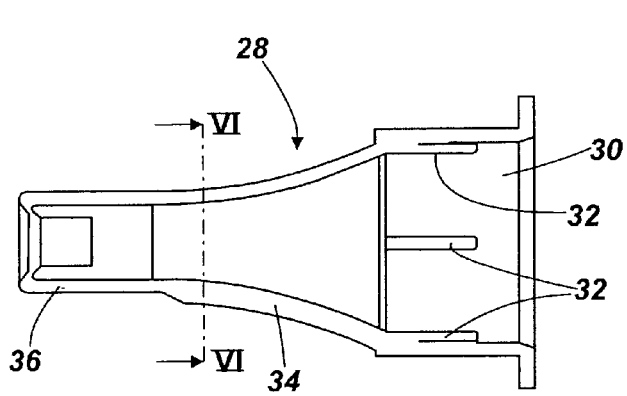
FIG. 3 is a longitudinal sectional view through an embodiment of a pen cap in accordance with this invention.
Figure 4:
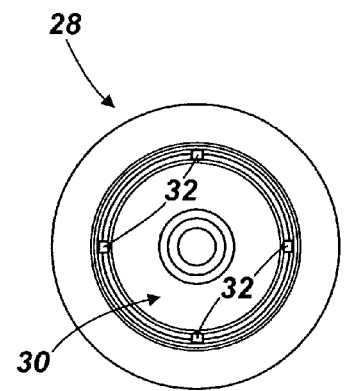
FIG. 4 is a rear end view on the pen cap.
Figure 5:
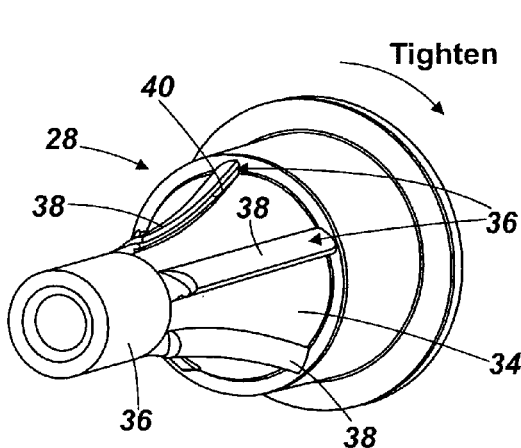
FIG. 5 is a general perspective view showing the differential friction ribs.
Figure 6:
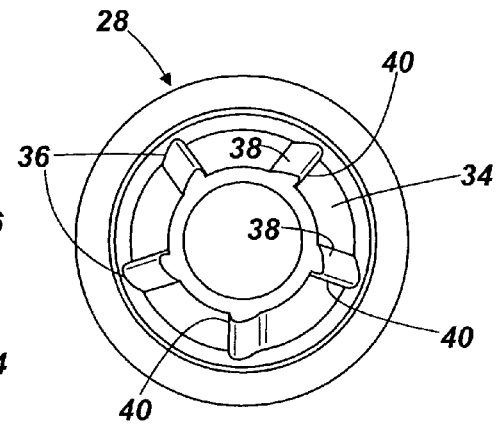
FIG. 6 is a section view through the cap taken on lines VI-VI of FIG. 3.

As seen more particularly in FIG. 2, the pen needle 24 comprises a moulded plastics collar with an internal thread (not shown) that can be threaded on to the threaded portion 22 of the cartridge holder 20, and having external splines 26.

Referring to FIGS. 3 to 6, the pen needle 24 is supplied in a sterile condition inside a pen cap 28. The pen cap 28 has an open end 30 defining a cylindrical socket with inwardly directed ribs 32 designed to slide between the splines 26 on the pen needle, so that torque applied to the pen cap is transmitted to the pen needle. The pen cap may be hermetically sealed by means of a foil closure or the like applied across a rear peripheral flange around the end 30. Forwardly the pen cap converges in a frustoconical grip portion 34 with a generally curved side and terminating in a closed generally cylindrical tip portion 36.

Externally, the frustoconical portion is provided with a series of angularly spaced ribs 36 designed so that the amount of torque that can be transmitted to the cap by a manual grip before slippage in the tightening direction (clockwise as viewed in FIG. 5) is less than that in the loosening direction. As can be seen more specifically in FIGS. 5 and 6, the ribs have smoothly curved flanks 38 at a relatively low angle of inclination facing the loosening direction whereas the flanks 40 facing the tightening direction are abrupt and corrugated. In this way, when the needle cap with needle inside it are applied to the cartridge holder 20 and screwed, the needle cap limits the amount of tightening torque that can applied and also ensures that, when gripped manually, the amount of torque that can be transmitted in the loosening direction is greater than that in the tightening direction.

Figure 8:
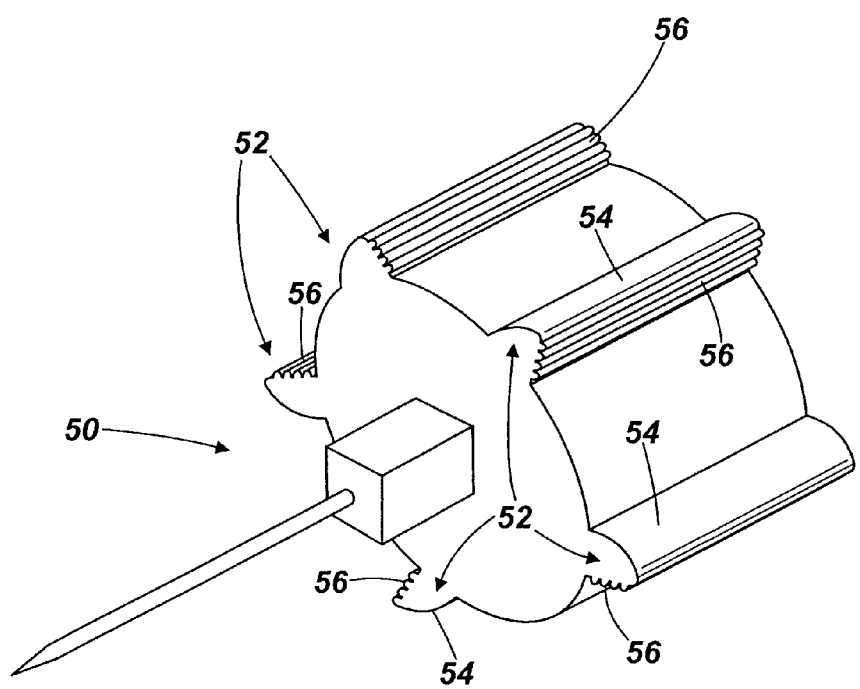
FIG. 8 is a general perspective view of an embodiment of needle tip with differential friction formations.

In the above embodiment the pen cap is supplied with a series of angularly spaced ribs 36 to provide differential friction characteristics in opposite series. In an alternative arrangement, as shown in FIG. 8, a pen cap 50 may be provided with similar angularly spaced ribs 52 which are smoothly profiled on one flank 54 and abruptly profiled 56 on the other flank to provide similar differential friction characteristics.

The invention claimed is:

1. A needle cap assembly for an injection device (10-22), the assembly comprising:
   a pen needle (24) rotatably engagable with an injection device or an associated component, and having a forwardly projecting needle,
   a needle cap (28) removably engaged with said pen needle (24) in which said needle cap shrouds said forwardly projecting needle, said needle cap comprising i) a generally cylindrical base (30) portion with an open end (30) defining a socket, ii) a generally frustoconical portion (34) with a frustoconical exterior surface face, and iii) a reduced diameter apex portion (36),
   the generally cylindrical base (30) merging into the frustoconical portion (34) and the frustoconical portion (34) merging into the reduced diameter apex portion (36),
   a longitudinal length of the frustoconical portion (34) being greater than a longitudinal length of the cylindrical base (30) and greater than a longitudinal length of the reduced diameter apex portion (36),
   the pen needle (24) and the needle cap (28) having complementary drive surfaces to allow rotation of the needle cap to be transmitted to said pen needle, and
   a manual gripping region comprising a series of angularly spaced, outwardly projecting ribs (36) provided on the exterior surface of the frustoconical portion (34) of said needle cap (28), wherein the gripping region accepts a first amount of torque that is transmitted to the needle cap by a manual grip on the gripping region before slippage in a tightening direction, the first amount of torque being less than a second amount of torque accepted on the gripping region in a loosening direction to loosen the pen needle, wherein,
   the projecting ribs (36) each have a generally smooth, relatively low friction surface (38) facing in the loosening direction and a relatively high friction surface (40) facing in the tightening direction that limit the amount of tightening torque that can applied to ensure that, when gripped manually by a user, the amount of torque that can be transmitted in the loosening direction is greater than the amount of torque that can be transmitted in the tightening direction.

2. A needle cap assembly according to claim 1, wherein the low friction surface (38) on each rib (36) is curved.

3. A needle cap assembly according to claim 2, wherein said relatively high friction surface (40) is grooved or corrugated.

4. A needle cap assembly according to claim 1, wherein said relatively high friction surface (40) extends generally radially.

5. A needle cap assembly according to claim 4, wherein said relatively high friction surface (40) is grooved or corrugated.

6. A needle cap assembly according to claim 1, wherein said relatively high friction surface (40) is grooved or corrugated.

7. The needle cap assembly of claim 1, wherein,
   the ribs have smoothly curved first flanks (38) at an angle of inclination facing in the loosening direction and corrugated second flanks (40) facing in the tightening direction, the angle of the first flanks being less than the angle of the second flanks.

8. The pen needle of claim 1, wherein the complementary drive surfaces of the needle cap and the pen needle comprise:
   i) external splines (26) running in a longitudinal direction of an outer surface portion of said pen needle (24), and
   ii) inwardly directed ribs (32) within the socket defined by the cylindrical base (30) portion, the inwardly directed ribs (32) engagable with the external splines (26) so that torque applied to the pen cap is transmitted to the pen needle, the inwardly directed ribs (32) being limited to the cylindrical base (30) portion and not extending into the frustoconical portion (34).

9. The pen needle of claim 8, wherein,
   the outwardly projecting ribs provided on the exterior surface of the frustoconical portion (34) of said needle cap (28) are separate from other exterior portions of the of said needle cap (28) that are free of the outwardly projecting ribs, and
   all of the outwardly projecting ribs together comprise a first overall portion of the exterior surface of the frustoconical portion (34) of said needle cap (28) and all of the portions of the exterior surface of the frustoconical portion (34) of said needle cap (28) that are free of the outwardly projecting ribs together comprise a second portion of the exterior surface of the frustoconical portion (34) of said needle cap (28), the second portion being greater than the first portion,
   wherein the outwardly projecting ribs (36) provided on the exterior surface of the frustoconical portion (34) of said needle cap (28) are limited to the frustoconical portion (34) of said needle cap (28) such that the cylindrical base (30) is free of the outwardly projecting ribs (36).

10. The pen needle of claim 1, wherein,
   the outwardly projecting ribs provided on the exterior surface of the frustoconical portion (34) of said needle cap (28) are separate from other exterior surface portions of of said needle cap (28) that are free of the outwardly projecting ribs, and all of the outwardly projecting ribs together comprise a first overall portion of the exterior surface of the frustoconical portion (34) of said needle cap (28) and all of the portions of the exterior surface of the frustoconical portion (34) of said needle cap (28) that are free of the outwardly projecting ribs together comprise a second portion of the exterior surface of the frustoconical portion (34) of said needle cap (28), the second portion being greater than the first portion,
wherein the outwardly projecting ribs (36) provided on the exterior surface of the frustoconical portion (34) of said needle cap (28) are limited to the frustoconical portion (34) of said needle cap (28) such that the cylindrical base (30) is free of the outwardly projecting ribs (36).

11. A needle cap assembly according to claim 1, wherein the outwardly projecting ribs (36) provided on the exterior surface of the frustoconical portion (34) of said needle cap (28) are limited to the frustoconical portion (34) of said needle cap (28) such that the cylindrical base (30) is free of the outwardly projecting ribs (36).

12. A needle cap assembly as claimed in claim 1, wherein each outwardly projecting rib extends longitudinally along the gripping region.

13. A needle cap assembly for an injection device the assembly comprising:
a pen needle comprising
i) a moulded plastics hub with an internal thread for engaging a corresponding threaded portion of an autoinjection device, and a plurality of external splines, and
ii) a double ended needle having a rearwardly facing end for use in penetrating a septum in the end of the cartridge, and a forwardly projecting end for use in penetrating flesh of a user; and
a needle cap (28) removably engaged with said pen needle (24) in which the needle cap shrouds said forwardly projecting end, the needle cap having
i) an open end defining a cylindrical socket with inwardly directed ribs designed to slide between the splines on the pen needle so that torque applied to the pen cap is transmitted to the pen needle, and to allow rotation of the needle cap to be transmitted to said pen needle, and
ii) an exterior surface, the exterior surface of the needle cap provided with a gripping region comprising a series of angularly spaced, outwardly projecting ribs provided on the exterior surface the ribs having a generally smooth low friction surface facing in a tightening direction and a textured high friction surface facing in a loosening direction such that, when gripped manually, the torque that can be applied to tighten the pen needle before the manual grip slips is less than that the torque that can be applied to loosen the pen needle.

14. A needle cap assembly as claimed in claim 13, wherein the textured high friction surface facing in the loosening direction comprises a grooved or corrugated surface.

15. A needle cap assembly as claimed in claim 13, wherein each outwardly projecting rib extends longitudinally along the gripping region.

16. A needle cap assembly as claimed in claim 15, wherein the needle cap further comprises a generally cylindrical base merging into a frustoconical portion and the frustoconical portion merging into a reduced diameter apex portion, the gripping region being provided on the exterior of the frustoconical portion.

17. A needle cap assembly as claimed in claim 13, wherein the low friction surface is curved and the high friction surface is generally radially extending.

18. A needle cap assembly as claimed in claim 17, wherein the low friction surface is at a relatively low angle of inclination facing the loosening direction.

19. A needle cap assembly for an injection device the assembly comprising:
a pen needle comprising
i) a moulded plastics hub with an internal thread for engaging a corresponding threaded portion of an autoinjection device and a plurality of external splines, and
ii) a double ended needle having a rearwardly facing end for use in penetrating a septum in the end of the cartridge and a forwardly projecting end for use in penetrating the flesh of a user; and
a needle cap (28) removably engaged with said pen needle (24) and shrouding said forwardly projecting end, the needle cap having
i) an open end defining a cylindrical socket with inwardly directed ribs designed to slide between the splines on the pen needle so that torque applied to the pen cap is transmitted to the pen needle and to allow rotation of the needle cap to be transmitted to said pen needle; and
ii) an exterior surface, the exterior surface of the needle cap being provided with a gripping region comprising a series of angularly spaced, outwardly projecting ribs provided on the exterior surface the ribs having a curved generally smooth low friction surface facing in a tightening direction and a generally radially extending high friction surface facing in the loosening direction such that, when gripped manually, the torque that can be applied to tighten the pen needle before the manual grip slips is less than the torque which can be applied to loosen the pen needle.

\* \* \* \* \*